United States Patent [19]
Barak et al.

[11] Patent Number: 5,084,064
[45] Date of Patent: Jan. 28, 1992

[54] SURGICAL CUFF

[75] Inventors: Jacob H. Barak, Oranit, Israel; Alan R. Millner, Lexington; Robert T. V. Kung, Andover, both of Mass.

[73] Assignee: ABIOMED Cardiovascular, Inc., Danvers, Mass.

[21] Appl. No.: 366,652

[22] Filed: Jun. 15, 1989

[51] Int. Cl.$^5$ ............................................. A61F 2/06
[52] U.S. Cl. ........................................................ 623/1
[58] Field of Search .................. 623/1, 3, 12; 606/151

[56] References Cited

U.S. PATENT DOCUMENTS

| | | | |
|---|---|---|---|
| 3,818,511 | 6/1974 | Goldberg et al. | 623/1 |
| 4,581,029 | 4/1986 | Joh | 623/3 |
| 4,650,486 | 3/1987 | Chareier | 623/3 |
| 4,888,009 | 12/1989 | Lederman et al. | 623/2 |
| 4,902,291 | 2/1990 | Kolff | 623/3 |
| 4,986,831 | 1/1991 | King et al. | 623/1 |

FOREIGN PATENT DOCUMENTS 0010865 5/1980 European Pat. Off. .............. 623/12

OTHER PUBLICATIONS

A New Connector System for Total Artificial Hearts, Holfert et al.
A Solution to Inlet Pannus Formation in the Pneumatic Artificial Heart, W. E. Pae, Jr. et al.

Primary Examiner—David J. Isabella
Assistant Examiner—Stephanie L. Iantorno
Attorney, Agent, or Firm—Lahive & Cockfield

[57] ABSTRACT

A vascular connector has a rough surfaced skirt which is trimmed to a size for surgical attachment, and a smooth central tube centrally extending through the skirt to a point upstream of the rough surface. A collar centrally affixed to the skirt releasably engages the tube, which in turn may be fabricated as a permanently attached input conduit of a total artificial heart. For installing the connectors, a skeletal frame fixture secures the central tubes or collars of plural connectors in defined positions corresponding to the attachment ports of the intended pump device.

6 Claims, 2 Drawing Sheets

5,084,064

SURGICAL CUFF

BACKGROUND OF THE INVENTION

The present invention relates to surgical cuffs of the type used for forming a fluid-tight connection to a blood vessel in the body of a human or animal subject. In particular, it relates to cuffs which are sutured to a major vessel and/or to tissue surrounding the vessel in order to establish a connection for a blood pumping mechanism such as a total artificial heart (TAH). One such structure, having a fabric suture ring attached to a stent which supports a valved flow tube, is shown in U.S. patent application Ser. No. 720,361 filed Apr. 5, 1985 of inventors David M. Lederman et al. Reference is made to that application for specific descriptions of material coatings and surface properties.

Atrial cuffs and vascular graft connector junctions, as well as mountings for valves which may be included in such structures, have been identified as primary locii for thrombus formation. This is due to many factors, including the surrounding fluid flow conditions, physical gaps and irregularities in the structures, and also the biocompatibility surface properties of the materials employed in such structures. In addition, occlusion of inflow openings of artificial heart devices has been observed due to pannus formation extending up to and into the openings.

The foregoing problems have been addressed by several approaches, including the precision formation of mating structural elements to eliminate gaps; the micro-finishing of exposed surfaces to discourage microembolus formation, and the selection of appropriately biocompatible materials. Nonetheless thrombogenesis, thromboembolism and device flow obstruction remain as major potential problems in heart device surgery.

SUMMARY OF THE INVENTION

Accordingly, it is desirable to control one or more of these problems.

This is achieved in accordance with the principles of the present invention by providing a vascular connector having a rough skirt or membrane for suturing to biological tissue, and a smooth tubular passage centrally entering the skirt. In an illustrative embodiment as an atrial cuff which provides an inlet to an artificial heart, the rough skirt has a first side formed of a double velour surgical dacron fabric, which faces the atrium and encourages permanent thrombus attachment and growth of the pseudointima, and has a second side coated with a biocompatible silicone compound which resists tissue growth and penetration by bodily fluids. The central tube has a smooth surface of biologically inert polymer, and extends upstream of the rough skirt. With this construction, pannus formation is restricted to the rough skirt portion, and stops abruptly at the wall of the smooth tube. In addition, flow irregularities are avoided near the junction of the connection, due to the formation of pseudointima which incorporates any locally clinging thrombus, so that the principal conditions responsible for thromboembolism and occlusion are reduced or eliminated.

Preferably, a collar ring is affixed to the skirt, and the central tube is a separate element, which may, for example, be attached to an artificial heart or other pump device, that separably attaches by a clamp, screw threads or locking detent to the collar. When used with such a pump device, the connector is sutured to surrounding tissue while held in a jig that maintains two or more vascular connectors in a fixed spatial relationship corresponding to the pump's several ports. This allows the pump device to be readily connected, after suturing of the connector skirt to tissue, without stretching or deforming the tissue, or crimping the flow tubing, and allows the pump to be replaced without removing or replacing sutures.

BRIEF DESCRIPTION OF THE DRAWINGS

These and other features of the invention will be understood from the following detailed description of an illustrative embodiment, which will be understood in light of the existing knowledge of materials and constructions, taken together with the skills and techniques commonly employed by workers in the field of this invention, and which is illustrated in particularity by the drawings herein.

DETAILED DESCRIPTION

Figure 1:
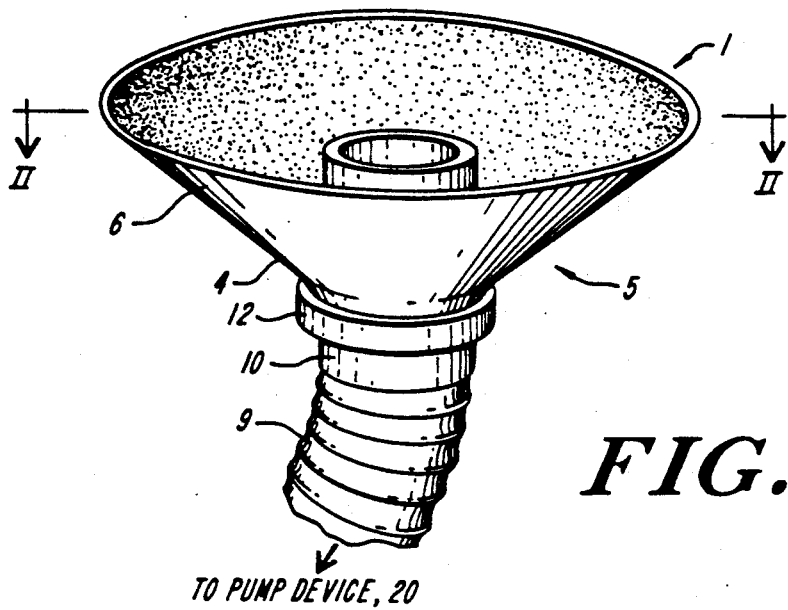
FIG. 1 is a perspective view of an atrial cuff in accordance with a preferred aspect of the invention.

As shown in FIG. 1 a cuff 1 in accordance with the present invention provides a structure for connecting a fluid inflow, in this case the atrium of the natural heart, to an artificial heart. Cuff 1 has a skirt 5 surrounding a central tube 10. Skirt 5 is formed of a flexible material in a general disk-like or conical shape adapted to be trimmed by a surgeon to fit the atrial remnants of the natural heart, in the region where the tricuspid or mitral valves were located prior to heart removal. Skirt 5 extends from a central region 4 to a peripheral edge 6 which, after trimming, is surgically attached to the atrial remnants by appropriate surgical techniques, such as suturing. The central tube 10 passes through the central region 4 and defines a passage for blood between the atrium and the pump device. The tube 10 has an essentially smooth surface, as discussed further below, and an inner diameter effective to assure adequate flow with minimal pressure drop at the pumping rates characteristic of the heart device. Visible at 12 is a collar ring which in the illustrated preferred embodiment is permanently affixed to the skirt and constitutes a fluid-tight connection fitting that releaseably couples to the tube 10. Tube 10, in turn, is preferably the end fitting of a conduit 9 connected to a heart pump 20, not shown. This tube may incorporate a valve which allows the heart pump to create unidirectional flow.

Figure 2:
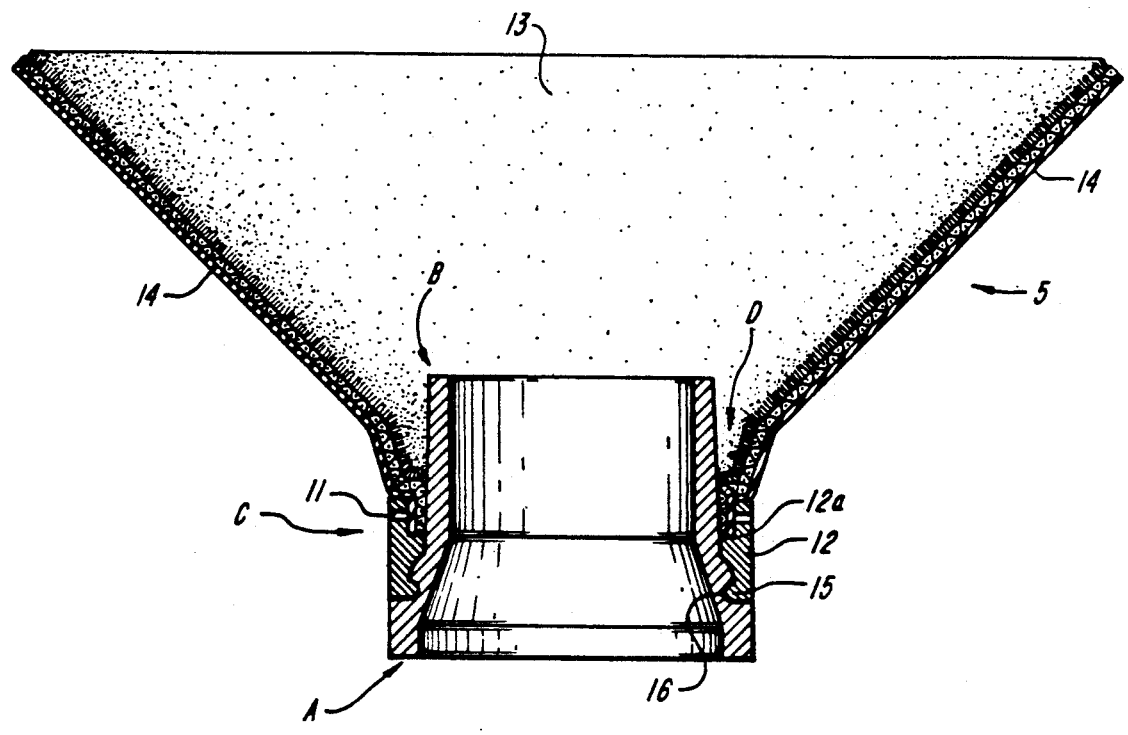
FIG. 2 is a cross-sectional view of the cuff of FIG. 1.

FIG. 2 is a vertical section through the connector 1 of FIG. 1, illustrating in greater detail the preferred structure of the skirt 5, collar 12 and tube 10. Skirt 5 has a first surface 13 which constitutes an "inner" surface facing the vessel interior, and which therefore is, in use, in contact with a flow of blood, and a second surface 14 constituting an "outer" surface which normally contacts other biological fluids. Surface 13 is a rough surface, such as a double velours surgical Dacron fabric, and surface 14 is a biologically inert smooth surface, such as a silicone elastomer, which is applied as a coating over the outside of the fabric. The outer coating serves as a barrier to prevent biological material from passing through the fabric into the bloodstream, and also acts as a sealant to resiliently seal about the suture connections which secure the skirt to surrounding tissue. The thickness of the outer coating is preferably one-quarter to one-half millimeter, and is effective to provide a substantially impermeable barrier as well as an effective seal at suture lines, although coatings as thin as 0.025 mm may be employed.

Tube 10 in a prototype design is a metal tube coated with a hemocompatible coating, such as a polyurethane, and is smoothly finished so that it does not promote microembolus formation or allow attachment of thrombus or tissue. Significantly, with the illustrated collar construction involving an external collar 12, tube 10 forms a single smooth conduit extending with no seams or mechanical junctions contacting the bloodstream, from a point A downstream of the cuff, past the neck of the cuff C, to a point B upstream of the rough inner cuff surface. Point B is at least 1.5 millimeters from, and may extend two to five millimeters or more upstream of, the rough surface region D.

With this construction, the rough inner surface promotes permanent thrombus attachment and the growth of normal pseudointima, while a clean transition is maintained at the neck region D. The edge of the tissue ingrowth region at D is removed from the flow region and from the vortex activity associated with the fluid conduit inlet region A, so this construction discourages both pannus formation and the generation of microemboli.

Still with reference to FIG. 2, the collar 12 is preferably formed as a thin ring having a shoulder 12a about which the skirt 5 is attached. The skirt may be attached by suturing, at suture holes 11, and gluing the fabric to the collar ring prior to applying the outer coating of impermeable smooth polymer. The ring may have a composite structure, for example, one employing a deformable thin band of 0.1 mm steel as an inner core within a coated or molded plastic body, and it preferably further includes means for securing the tube 10 therein. In the illustrated embodiment shown in the Figure, a protruding tooth or rim 15 extends from the collar and is positioned to engage a corresponding detent or groove 16 formed in the tube to assure that once the tube is inserted through ring 12, the tube is attached securely to the cuff structure. Alternative means of securing the collar and tube are also contemplated, including, for example, the provision of an external snap-ring, circle clip or tubing clamp about the collar. In the region D, the outer surface of the tubing 10 bears against the rough fabric surface 13, compressing it slightly and defining a clear, gap-free boundary between the two surfaces.

By way of illustration, the various components of the described atrial cuff have the following approximate dimensions:

| | |
|---|---|
| diameter of skirt, before trimming: | ten centimeters |
| inner diameter of tube: | twenty millimeters |
| tube wall thickness: | one millimeter |
| tube length: | two and one-half centimeters. |

For use as an inlet to an artificial heart or other blood pumping device, it is necessary that the atrial cuff, and any other vascular grafts or connectors according to the invention which constitute the inlets or outlets to the device, be located in positions to connect to the intended device. This essentially requires that the surgeon, in attaching each vascular connector to tissue, have a clear and exact sense of where each of the other connectors will lie.

Figure 3:
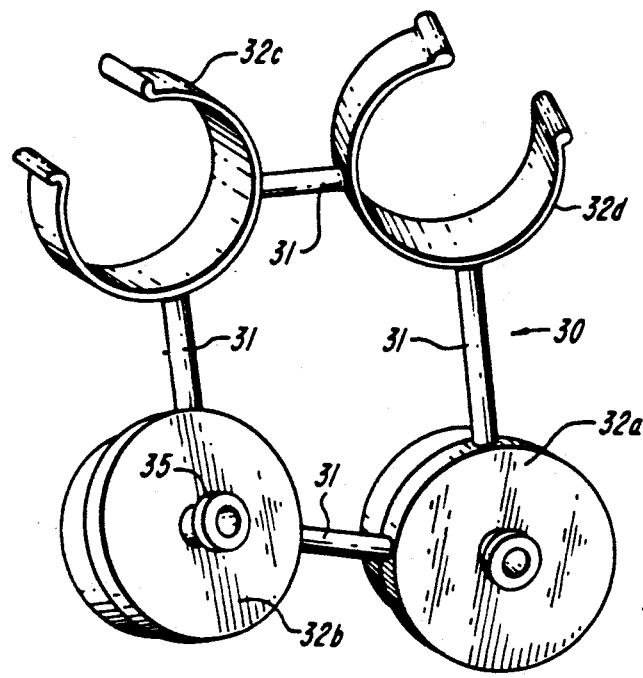
FIGS. 3 and 3A illustrate an alignment fixture which orients plural connectors for surgical installation.

In accordance with another aspect of the present invention, an alignment fixture is provided to temporarily hold each vascular connector in the exact position, in relation to the other connectors, to receive its corresponding fluid line of a blood pumping device. As shown in FIG. 3, one embodiment of such a device includes an ephemeral frame 30 which is a thin skeleton or bodyless wire-like element, having a number of arms 31 each extending to a connector holder 32a, 32b . . . 32d and which each grip a corresponding vascular connector, vessel or vascular graft to hold it in a fixed position and alignment. As shown, four holders of two types are provided to secure connectors at positions aligned with the ports of a pump unit, not shown. In general, the holders may consist of different structures suitable for the connectors employed, for example, of a flexible plug or tube which forms a friction fit within the opening of the above-described cuff collar element, or of a clamp which grips a vessel or the attached connector from outside.

In the embodiment of FIG. 3, holders 32a, 32b are plug-shaped with a sealing outer contour like that of the tube fitting 10 of the pump, while holders, 32c, 32d are external flexible clamps positioned to hold the pulmonary artery and aorta in position to receive their connections.

The thin frame alignment structure 30 permits the surgeon maximum access to the operative theater for effecting the necessary surgery and suture connections, while assuring that all connectors assume the precise positions necessary to receive the pump device without crimping or stretching of lines or tissue.

Further illustrated in FIG. 3 is a fluid fitting 35, drawn as a Luer fitting, which passes through the plug fitting 32a or 32b, and allows the installed cuff to be attached to a source of saline under pressure. This permits convenient testing of the fluid seal at the suture connections without the problems of access and excessive blood loss which would arise if pressure testing were performed with the heart pump installed.

Figure 3A:
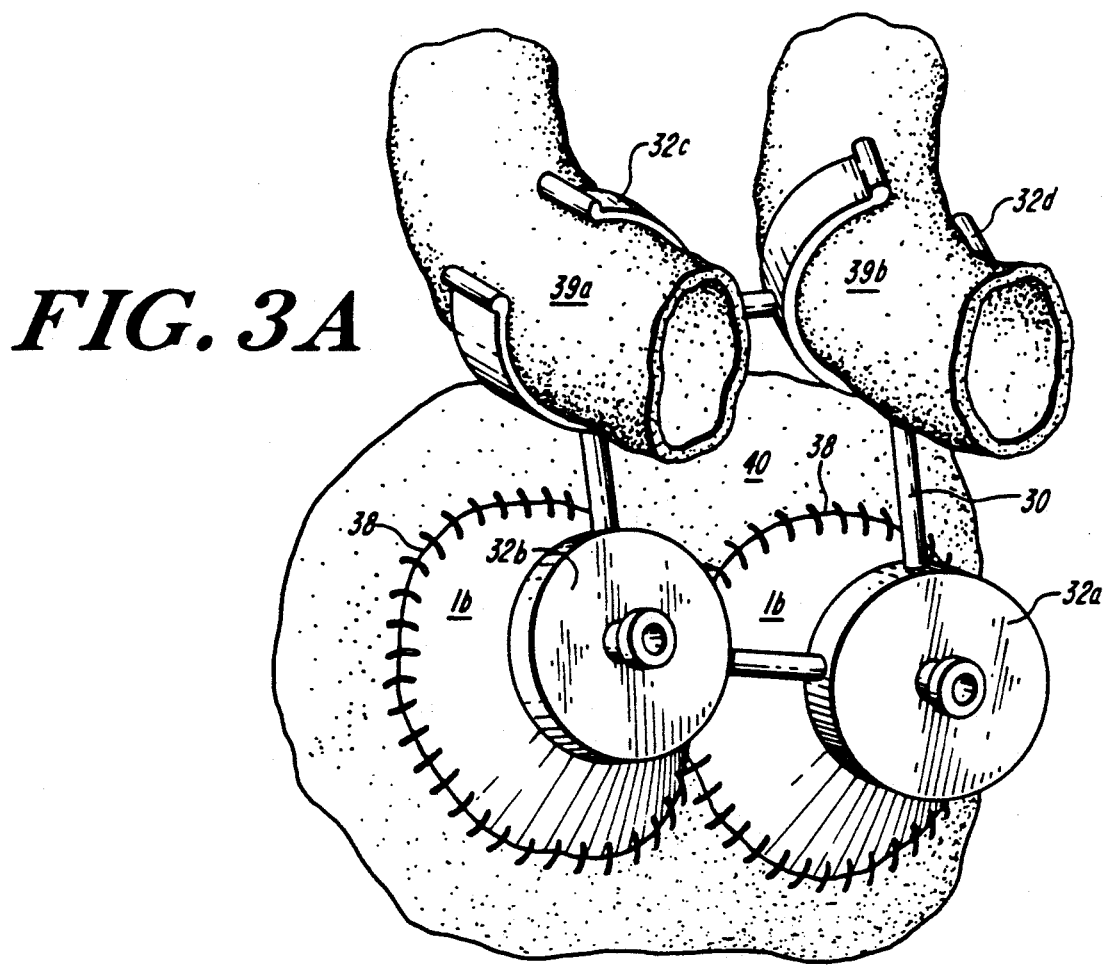

FIG. 3A illustrates, by way of completeness, the alignment fixture 30 in use. Each of the holders 32a, 32b is fitted into a cuff 1a, 1b, and both cuffs are sutured, at 38, to a remnant 40 of the atrium of the natural heart, in positions to couple with respective pump device inlets. The remaining holders 32c, 32d grip vessels 39a, 39b in positions to couple with the pump device outlets.

It will be understood that the present invention has been described with reference to the particularly demanding application of an atrial cuff, wherein both tissue growth and the formation of microemboli have each been persistent problems, and with reference to a heart pump device for connection to the cuff. The invention is not, however, limited to the illustrated construction and may be adapted with appropriate modifications, to various other vascular connections known in the art, both as an inflow or an outflow vascular connector or graft. The invention further contemplates the described vascular connector structure with additional elements incorporated therein, such as one-way flap valves or microembolus filters. Further variations, and modifications obtained by substituting known equivalents for elements of the described devices, or applying routine skill and technical variations, are all considered to be within the scope of the invention, as set forth in the claims appended hereto.

What is claimed is:

1. A cuff structure for surgical attachment to define a fluid tight blood flow connection, such structure comprising
    a flexible skirt having inner and outer faces with a rough surface on the inner face and an impermeable biocompatible material on the outer face
    a collar centrally affixed to said skirt, and
    a flow tube centrally connected to and projecting through said skirt, said flow tube including a tube segment separably connected to said collar and having a portion which is smooth and non-thrombogenic, said portion projecting past said rough surface on said inner face
    whereby when the skirt is attached to tissue with said inner face facing a blood flow the cuff structure forms a non-occluding and non-thrombogenic blood flow connection.

2. A cuff structure according to claim 1, further comprising a valve in said tube segment.

3. A cuff structure according to claim 1, wherein said skirt is dimensioned for attachment to a human atrium.

4. A cuff structure according to claim 1, wherein said rough surface is formed of a surgical fabric.

5. A cuff structure according to claim 1, wherein said impermeable biocompatible material has an elastic property for forming a fluid tight seal about sutures passing therethrough.

6. A cuff structure according to claim 1, wherein said tube segment is connected to the collar by a releasable detent.

* * * * *